US008748411B2

(12) United States Patent
Rodriguez Fernandez et al.

(10) Patent No.: US 8,748,411 B2
(45) Date of Patent: Jun. 10, 2014

(54) ANTINEOPLASTIC COMPOUNDS AND PHARMACEUTICAL COMPOSITIONS THEREOF

(75) Inventors: Rolando Eduardo Rodriguez Fernandez, Ciudad de la Habana (CU); Roberto Vera Alvarez, La Habana (CU); Ania De La Nuez Veulens, Ciudad de la Habana (CU); Yuliet Mazola Reyes, La Habana (CU); Silvio Ernesto Perea Rodriguez, Ciudad de la Habana (CU); Boris Ernesto Acevedo Castro, Ciudad de la Habana (CU); Alexis Musacchio Lasa, Provincia la Habana (CU); Raimundo Ubieta Gómez, Ciudad de la Habana (CU)

(73) Assignee: Centro de Ingenieria Genetica y Biotechnologia, Ciudad de la Habana (CU)

( * ) Notice: Subject to any disclaimer, the term of this patent is extended or adjusted under 35 U.S.C. 154(b) by 1143 days.

(21) Appl. No.: 11/920,031

(22) PCT Filed: May 5, 2006

(86) PCT No.: PCT/CU2006/000002
§ 371 (c)(1),
(2), (4) Date: Jan. 6, 2009

(87) PCT Pub. No.: WO2006/119713
PCT Pub. Date: Nov. 16, 2006

(65) Prior Publication Data
US 2009/0215730 A1      Aug. 27, 2009

(30) Foreign Application Priority Data

May 12, 2005  (CU) ..................................... 2005-091

(51) Int. Cl.
| | |
|---|---|
| *A61K 31/66* | (2006.01) |
| *A61K 31/53* | (2006.01) |
| *A61K 31/505* | (2006.01) |
| *A61K 31/47* | (2006.01) |
| *A61K 31/415* | (2006.01) |
| *A61K 31/40* | (2006.01) |
| *C07D 251/42* | (2006.01) |
| *C07D 473/00* | (2006.01) |
| *C07D 239/02* | (2006.01) |
| *C07D 215/38* | (2006.01) |
| *C07D 235/00* | (2006.01) |
| *C07D 233/96* | (2006.01) |
| *C07D 209/14* | (2006.01) |
| *C07D 307/02* | (2006.01) |
| *C07D 229/00* | (2006.01) |
| *C07F 9/02* | (2006.01) |
| *C07C 281/02* | (2006.01) |
| *C07C 273/02* | (2006.01) |
| *C07C 303/00* | (2006.01) |
| *C07C 241/00* | (2006.01) |

(52) U.S. Cl.
USPC ........... 514/115; 514/245; 514/274; 514/313; 514/390; 514/416; 544/211; 544/276; 544/316; 544/317; 544/171; 548/309.7; 548/318.1; 548/505; 548/493

(58) Field of Classification Search
USPC ......... 514/115, 245, 274, 313, 390, 416, 471, 514/489, 586, 588, 590, 608, 644, 645; 544/211, 276, 316, 317, 171; 562/565, 562/14, 34, 47, 59; 564/83, 246, 310, 512
See application file for complete search history.

(56) References Cited

U.S. PATENT DOCUMENTS

| | | | |
|---|---|---|---|
| 2,673,859 A | 3/1954 | Simons | |
| 6,962,698 B1 * | 11/2005 | Peled et al. | ................ 424/93.7 |

FOREIGN PATENT DOCUMENTS

EP      1491553 A1    12/2004

OTHER PUBLICATIONS

Vijarpurkar et al. Molecular and Cellular Biology (2004)3827-3837.*
NIST (1999); 1-3.*
Calvin et al. Hepatology 2003 38(6):1540 (Abstract only).*
Narayanan et al (J. Nutr. 131:1427-1432 (2001).*
Perea, A. E. et al., "Antitumor Effect of a Novel Proapoptotic Peptide that Impairs the Phosphorylation by the Protein Kinase 2 (Casein Kinase 2)," Cancer Research, vol. 64, Oct. 1, 2004, pp. 7127-7129, XP002399575.
Johnson, T.P. et al., "The Synthesis of Potential Anticancer Agents. XXXVI. N-Nitrosoureas. II. Haloalkyl Derivatives," Journal of Medicinal Chemistry, American Chemical Society, Washington, US, vol. 9, No. 6, 1966, pp. 892-910, XP000929924.
Martinez, A.P. et al., "Some Semicarbazones and Thiosemicarbazones," J. Med. Chem., vol. 10, 1967, p. 1192, XP009072473.
Cates, L.A., "Phosphorous-Nitrogen Compounds. VII. Urea, Aziridinecarboxamide, and Semicarbazide Derivatives," Journal of Medicinal Chemistry, American Chemical Society, Washington, US, vol. 10, No. 5, 1967, pp. 924-927, XP001189240.
Kharasch, M.S. et al., "Factors Influencing the Cours and Mechanism of Girignard Reactions. XVI. An Isomer of Isophorone-delta-3,5,5-Trimethylcyclohexenone," J. Am. Chem. Soc., vol. 67, 1945, pp. 128-130, XP002399576.
Gershbein, L.L. et al., "Reactions of Isopropyl Alcohol in the Presence of Catalysts Containing Magnesium Oxide," J. Am. Chem. Soc., vol. 69, 1947, pp. 2888-2893, XP002399577.

(Continued)

*Primary Examiner* — Shirley V Gembeh
(74) *Attorney, Agent, or Firm* — Hoffmann & Baron, LLP

(57) ABSTRACT

Chemical compounds derived by in silico molecular modelling, having a well defined structure suitable for the blocking of the phosphorylation event, through the specific interaction of the chemical with the Casein Kinase 2 enzyme substrate phosphorylation domain or it's neighbourhood. This invention comprises also the pharmaceutical compositions containing such compounds, and their use in the preparation of medicines or agents for the treatment of diseases or conditions related with neoplasic processes.

2 Claims, 1 Drawing Sheet

(56) References Cited

OTHER PUBLICATIONS

Zhao, X. et al., "An Approach to the Design of Molecular Solids. The Ureylenedicarboxylic Acids," J. Am. Chem. Soc., vol. 112, No. 18, 1990, pp. 6627-6634, XP002399578.

Kimel, W. et al., "The Rearrangement of Allyl-Type Esters of beta-Keto Acids," J. Am. Chem. Soc., vol. 65, 1943, pp. 1992-1997, XP002399579.

Sah, P.P.T. et al., "Thiosemicarbazide as a Reagent for the Identification of Aldehydes, Ketones, and Quinones," Recl. Trav. Chim., vol. 69, 1950, pp. 1545-1553, XP009072493.

Landquist, J.K. et al., "Oxidative Cyclisation of Ketone Thiosemicarbazones. Part II. Derivatives of Phenoxyacetone," J. Chem. Soc. C, 1970, pp. 323-324, XP009072561.

Meggio et al., "One-thousand-and-one substrates of protein kinase CK2?", The FASEB Journal, vol. 17, pp. 349-368 (Mar. 2003).

* cited by examiner

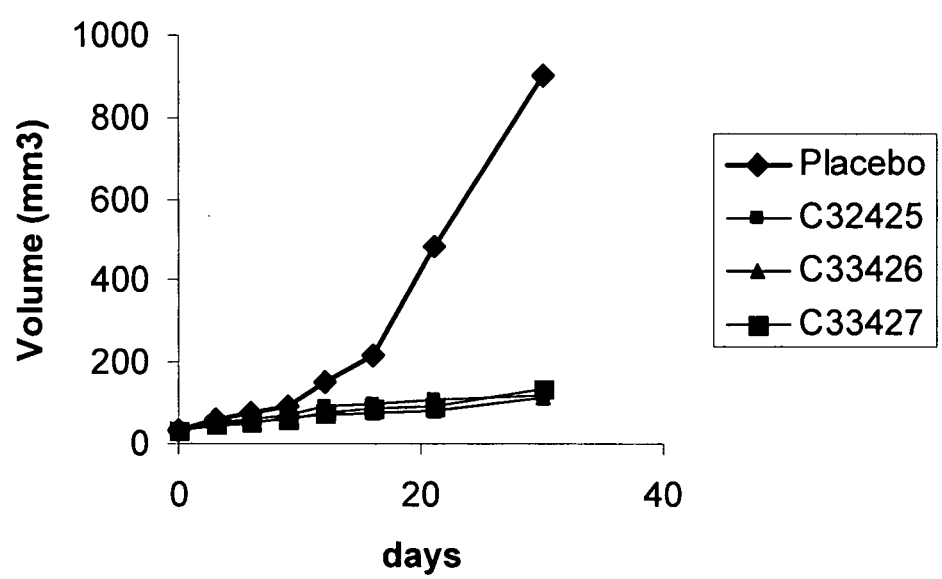

ANTINEOPLASTIC COMPOUNDS AND PHARMACEUTICAL COMPOSITIONS THEREOF

This application is the U.S. National Phase of, and Applicants claim priority from, International Application Number PCT/CU2006/000002 filed 5 May 2006 and Cuban Patent Application bearing Ser. No. CU 2005-091 filed 12 May 2005, which are incorporated herein by reference.

FIELD OF THE INVENTION

The present invention can be described into the field of molecular pharmacology particularly related with oncology, and more specifically with chemical compounds obtained by in silico molecular modelling, having a clear cytotoxic action and antitumoral effect by blocking the phosphorylation site on the Casein Kinase 2 substrates through their direct or indirect interaction, and the pharmaceutical compositions thereof.

BACKGROUND ART

Casein Kinase 2 (CK2) is a serine/threonine enzyme involved in the increment of the cell proliferation, being the nucleus it main intracellular location during the malignant transformation process. (Tawfic S., Yu S., Wang H., et al. (2001) Protein kinase CK2 signal in neoplasia. *Histol. Histopathol.* 16:573-582). Moreover some key viral proteins for the pathogeny of Human Immunodeficiency Virus (HIV) and of Hepatitis C Virus (HCV) have been reported as CK2 substrates (Meggio F., Marin O., et al. (2001) *Mol Cell Biochem* 227:145-151; Franck N., Le Seyec J., et al. (2005) Hepatitis C virus NS2 protein is phosphorylated by the protein kinase CK2 and targeted for degradation to the proteasome. *J Virol.* 79:2700-2008).

Findings of other groups worldwide, had also confirmed the existence of elevated levels of CK2 in different solid tumours of epithelial origin, in orders ranging from 3 to 7 times higher, respect to the normal tissue. (Tawfic S., Yu S., et al. (2001) Protein kinase CK2 signal in neoplasia. *Histol Histopatol.* 16:573-582; Faust R. A., Gapany M., et al (1996) Elevated protein kinase CK2 activity in chromatin of head and neck tumors: association with malignant transformation. *Cancer Letters* 101:31-35), besides the phosphorylation activity of the CK2 enzyme being a very important event in the malignant transformation of the cells it constitutes a strong marker on the tumour progression, (Seldin D. C., Leder P. (1995) Casein Kinase IIα transgene-induced murine lymphoma: relation to theileroiosis in cattle. *Science* 267:894-897), the over expression of CK2 on the other hand leads to the tumorigenesis of mammary cells by the up regulation in the signalling cascade Wnt/beta-catenin (Landesman-Bollag E., Romien-Mourez R., et al (2001) Protein Kinase CK2 in mammary gland tumorigenesis. *Oncogene* 20:3247-3257). Recent findings also suggested that CK2 plays an essential role in some other processes like chromatin remodelling (Barz T., Ackenmann K., et al. (2003) Genome-wide expression screens indicate a global role for protein kinase CK2 in chromatin remodelling. *J Cell Sci.* 116:1563-1577) and the regulation of cell survival (Unger G. M., Davis A. T., Slaton J. W., Ahmed K. (2004) Protein kinase CK2 as regulator of cell survival: implications for cancer therapy. *Curr Cancer Drug Targets,* 4:77-84). Of paramount importance for the understanding of the cancer development process, had been the findings proving that CK2 mediated phosphorylation is a very strong signal for cell survival, therefore considering this enzyme as an antiapoptotic mediator for the cell physiology (Ahmed K., Gerber D. A., Cochet C. (2002) Joining the cell survival squad: an emerging role for protein kinase CK2. *Trends Cell Biol,* 12:226-229; Torres J., Rodriguez J., et al (2003) Phosphorylation-regulated cleavage of the tumour suppressor PTEN by caspase-3: implications for the control of protein stability and PTEN-protein interactions. *J Biol Chem,* 278:30652-60).

On the basis of the foregoing findings, the CK2 mediated phosphorylation has been confirmed as a biochemical event, suitable to be used as a potential target for the therapeutic intervention on cancer, rendering all potential inhibitors of such event as prospective candidates for the treatment of such condition. Up to date several research groups worldwide have been developing different strategies to inhibit CK2 mediated phosphorylation with two experimental approaches: a) The direct inhibition of the CK2 enzyme, or b) The blocking of the phosphorylation site near to the acidic domain described as common to all CK2 substrates.

For both approaches, the authors have been able to demonstrate the concept by which the inhibition of the CK2 mediated phosphorylation event, yield to the induction of apoptosis on tumour cells, which implies an experimental validation of CK2 as a very promissory target in the finding of drugs for cancer treatment.

Example of the latter is a direct inhibitor of the enzyme like the 4,5,6,7-tetrabromotriazole (TBB) tested as a potent apoptosis and caspase dependent degradation inducer in Jurkat cells on the micro molar concentration range. (Ruzzene M., Penzo D., Pinna L. (2002) Protein kinase CK2 inhibitor 4,5,6,7-tetrabromobenzotriazole (TBB) induces apoptosis and caspase-dependent degradation of haematopoietic lineage cell-specific protein 1 (HS1) in Jurkat cells. *Biochem J.,* 364:41-47). Also, by inhibiting the expression of the CK2 enzyme by using anti-sense oligonucleotides, an in vitro apoptotic effect and antitumoral action in an experimental cancer model in mice. (Guo C., Yu S., et al. (2001) A potential role of nuclear matrix-associated protein kinase CK2 in protection against drug-induced apoptosis in cancer cells. *J Biol Chem,* 276:5992-5999; Slaton J. W., et al. (2004) Induction of apoptosis by antisense CK2 in human prostate cancer xenograft model. *Mol Cancer Res.* 2:712-721).

Other compounds like antraquinone derivatives, flavonoids, and halogenated azobenzylimidazoles have been described as CK2 ATP binding site inhibitors (Sarno S., et al. (2002) Toward the rational design of protein kinase casein kinase-2 inhibitors. *Pharmacol Therapeutics* 93:159-168), and 5-oxo-5,6-dihidroindolo(1,2-a)quinazolin-7-yl acetic acid (IQA) have been reported as a selective CK2 inhibitor using high throughput screening, (Vangrevelinghe E., et al. (2003) Biochemical and three-dimensional-structural study of the specific inhibition of protein kinase CK2 by [5-oxo-5,6-dihydroindolo-(1,2-a)quinazolin-7-yl]acetic acid (IQA). *J. Med. Chem.* 46:2556-2662).

The aforementioned compounds have shown their CK2 activity inhibiting effect in the micro molar range for the Inhibitory Concentration 50 (IC50), but no evidences have been reported of any antitumoral action in experimental models of cancer.

The other approach to inhibit the CK2 activity have been to interfere with the phosphorylation site on the substrate, in the patent application WO 03/054002 and the work of Perea S. E et al. (2004) Antitumor effect of a novel proapoptotic peptide impairing the phosphorylation by the protein kinase CK2. *Cancer Res.* 64:7127-7129, the authors are limited to propose the use of a cyclic peptide family to block the CK2 mediated phosphorylation on the substrate site, showing tumour cell cytotoxicity and antitumoral effect in cancer pre-clinical models. However the described peptides have the limitation of not being able per se to penetrate into the cells, hence requiring a membrane permeation peptide being fused to them.

In general terms, when compared to small molecules, the use of peptides have the drawbacks of a decreased in vivo stability in the circulation, degradation, being very difficult to formulate in oral administration and they are not easily transported inside the cells. (Ludger Wess, Isogenica: Improving peptides, Biocentury Oct. 25, 2004). Other problems of peptides widely described in the literature are the faster clearance, their immunogenic potential, and their cost per therapeutic dose is known to be generally superior to non-peptidic drugs.

SUMMARY OF THE INVENTION

Taking into account the potential limitations for the usage of the aforementioned cyclic peptides as candidate therapeutic agents, the present invention describes, in fact as the first time, chemical molecules capable of inhibiting the CK2 mediated phosphorylation by direct or indirect interaction with the phosphorylation site on the enzyme substrate, and elicit the cytotoxicity and antitumoral effect in experimental model of cancer.

The chemical compounds hereby described have a well defined chemical structure allowing them to accomplish one or several of the following actions:

A: allows the binding of the compound to the substrate phosphorylation site, blocking in a direct or indirect manner the binding of the CK2 enzyme to the substrate.

B: allows the binding of the compounds to the substrate phosphorylation domain, still permitting the CK2 enzyme binding but blocking in a direct or indirect manner the transfer of the phosphate group to the phosphoacceptor serine.

C: allows the binding of the compounds to the CK2 substrate protein, eliciting a conformational change in the phosphorylation domain, its neighbourhood, or both, in such a manner that it blocks directly or indirectly the binding of the CK2 enzyme or the transfer of the phosphate group to the phosphoacceptor serine.

Therefore the described compounds are mainly characterized by their capacity of inhibition of the biochemical event of CK2 mediated phosphorylation.

In a particular realization, this invention refers to chemical molecules characterized by a particular chemical structure defined by the occurrence in any part of the molecule, of some chemical elements bound in a consecutive manner, with the indicated electronic hybridization and grouped into the following five structural groups:

I. N—[C(sp2)]$_{1,2,3}$-N
II. N—[C(sp2)]$_{1,2}$-[C(sp3)]$_{1,2,3}$-N
III. N—[C(sp3)]$_{1,2,3}$-N
IV. N—C(sp2)-[C(sp3)]$_{1,2}$-C(sp2)-N
V. N—C(sp3)-[C(sp2)]$_{1,2}$-C(sp3)-N

Several compounds belonging to such structural classes are shown below:

1.

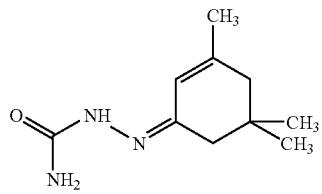

$C_{30401}$ (1Z)-3,5,5-trimethylcyclohex-2-en-1-one semicarbazone

2.

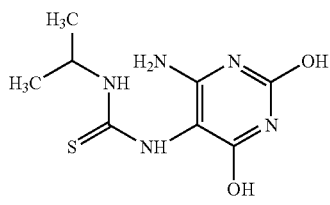

$C_{30402}$

N-(4-amino-2,6-dihydroxypyrimidin-5-yl)-N'-isopropylthiourea

3.

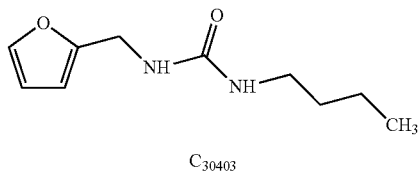

$C_{30403}$

N-butyl-N'-(2-furylmethyl)urea

4.

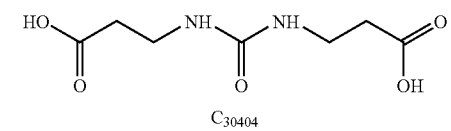

$C_{30404}$ 3-({[(2-carboxyethyl)amino]carbonyl}amino)propanoic acid

5.

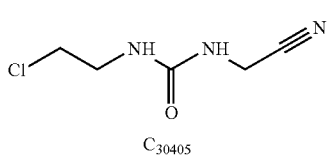

$C_{30405}$ 1-(2-chloroethyl)-3-(cyanomethyl)urea

6.

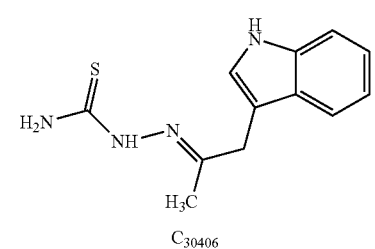

$C_{30406}$ (2E)-1-(1H-indol-3-yl)acetone thiosemicarbazone

7.

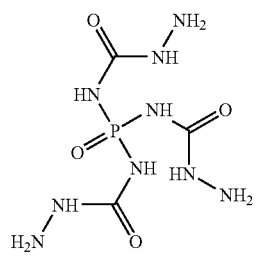

$C_{30407}$

N,N',N''-phosphoryltrihydrazinecarboxamide

-continued

8.

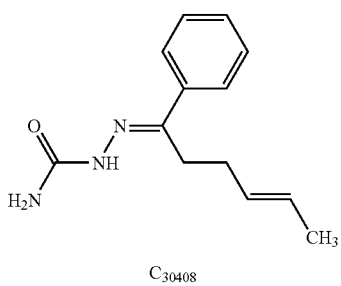

C30408

(1E,4E)-1-phenylhex-4-en-1-one semicarbazone

9.

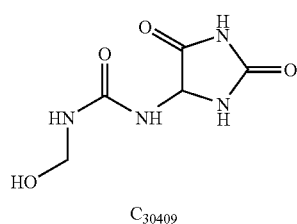

C30409

1-(2,5-dioxoimidazolidin-4-yl)-3-(hydroxymethyl)urea

10.

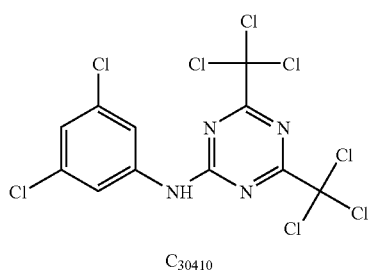

C30410

N-(3,5-dichlorophenyl)-4,6-bis(trichloromethyl)-1,3,5-triazin-2-amine

11.

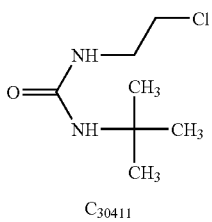

C30411

1-tert-butyl-3-(2-chloroethyl)urea

12.

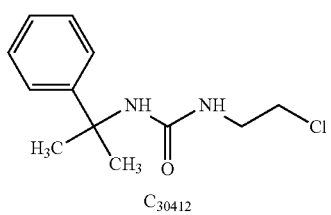

C30412

1-(2-chloroethyl)-3-(1-methyl-1-phenylethyl)urea

-continued

13.

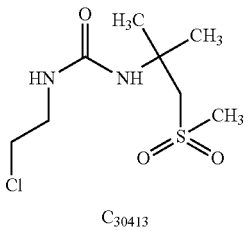

C30413

1-(2-chloroethyl)-3-[1,1-dimethyl-2-(methylsulfonyl)ethyl]urea

14.

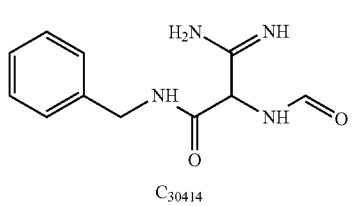

C30414

3-amino-N-benzyl-2-(formylamino)-3-iminopropanamide

15.

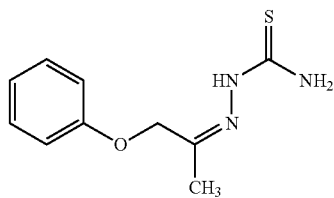

C30415

(2Z)-1-phenoxyacetone thiosemicarbazone

16.

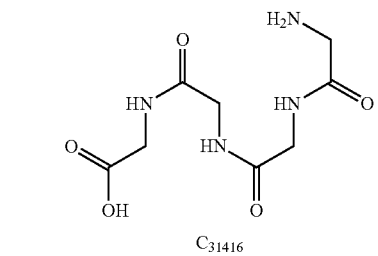

C31416

{[({[(aminoacetyl)amino]acetyl}amino)acetyl]amino}acetic acid

17.

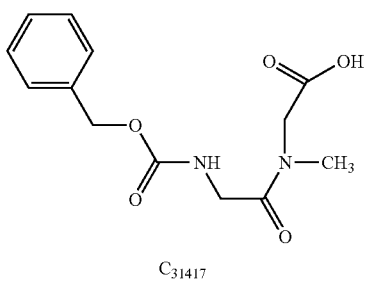

C31417

[({[(benzyloxy)carbonyl]amino}acetyl)(methyl)amino]acetic acid

18.

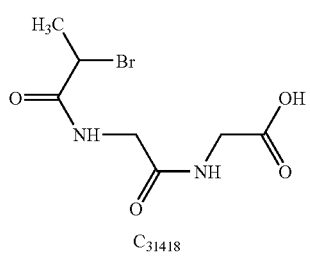

C<sub>31418</sub>

({[(2-bromopropanoyl)amino]acetyl}amino)acetic acid

19.

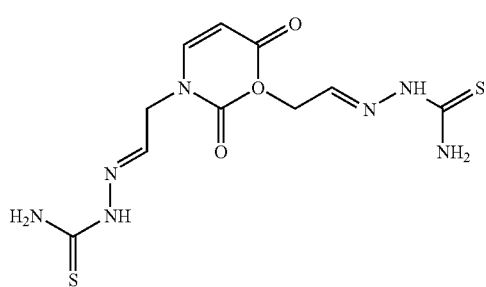

C<sub>31419</sub>

(1E,1'E)2,2'-(2,4-dioxopyrimidine-1,3(2H,4H)-diyl)diacetaldehyde dithiosemicarbazone

20.

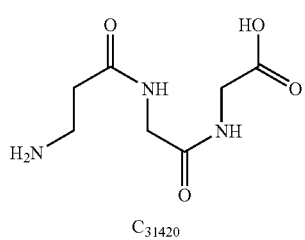

C<sub>31420</sub>

({[(3-aminopropanoyl)amino]acetyl}amino)acetic acid

21.

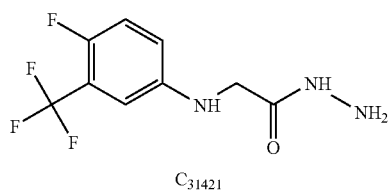

C<sub>31421</sub>

2-{[4-fluoro-3-(trifluoromethyl)phenyl]amino}acetohydrazide

22.

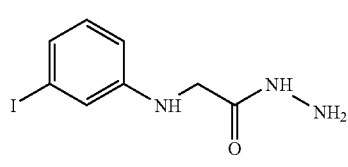

C<sub>31422</sub>

2-[(3-iodophenyl)amino]acetohydrazide

23.

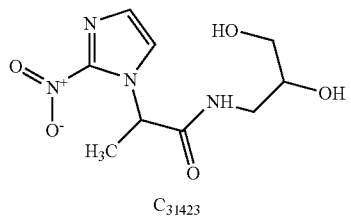

C<sub>31423</sub>

N-(2,3-dihydroxypropyl)-2-(2-nitro-1H-imidazol-1-yl)propanamide

24.

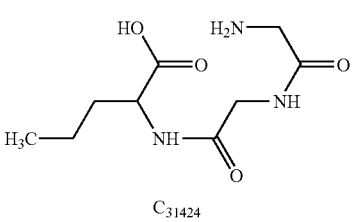

C<sub>31424</sub>

2-({[(aminoacetyl)amino]acetyl}amino)pentanoic acid

25.

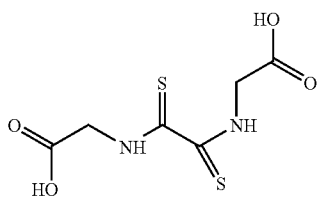

C<sub>32425</sub>

2,2'-[(1,2-dithioxoethane-1,2-diyl)diimino]diacetic acid

26.

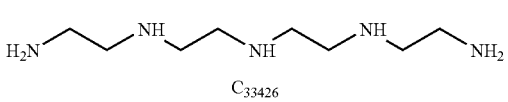

C<sub>33426</sub>

N-(2-aminoethyl)-N'-{2-[(2-aminoethyl)amino]ethyl}ethane-1,2-diamine

27.

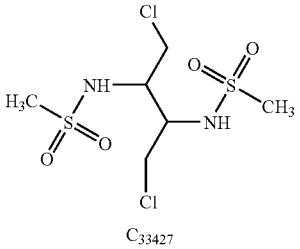

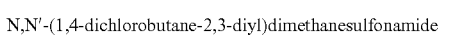

C<sub>33427</sub>

N,N'-(1,4-dichlorobutane-2,3-diyl)dimethanesulfonamide

28.

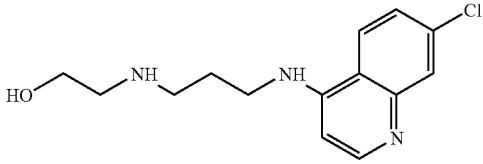

C<sub>34428</sub>

2-({3-[(7-chloroquinolin-4-yl)amino]propyl}amino)ethanol

29.

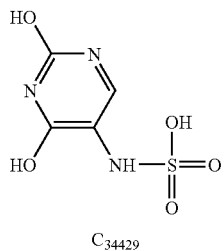

C₃₄₄₂₉

(2,4-dihydroxypyrimidin-5-yl)sulfamic acid

30.

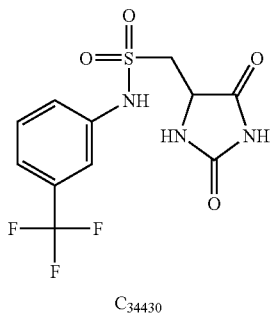

C₃₄₄₃₀

1-(2,5-dioxoimidazolidin-4-yl)-N-[3-(trifluoromethyl)phenyl]methanesulfonamide

31.

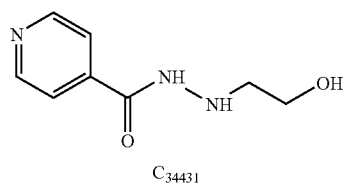

C₃₄₄₃₁

N'-(2-hydroxyethyl)isonicotinohydrazide

32.

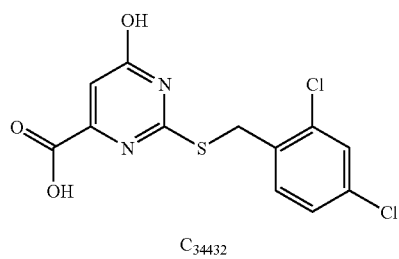

C₃₄₄₃₂

2-[(2,4-dichlorobenzyl)thio]-6-hydroxypyrimidine-4-carboxylic acid

33.

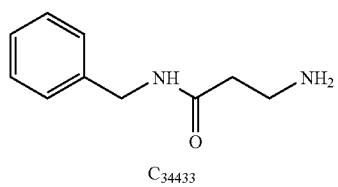

C₃₄₄₃₃

3-amino-N-benzylpropanamide

34.

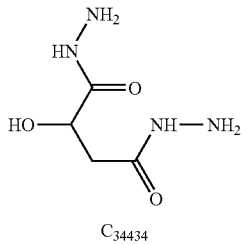

C₃₄₄₃₄

2-hydroxysuccinohydrazide

35.

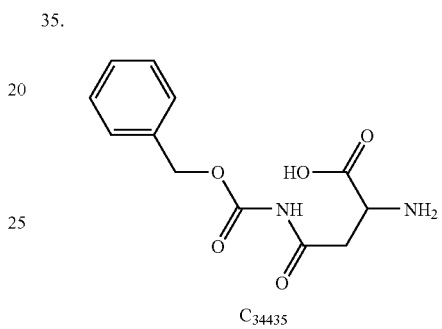

C₃₄₄₃₅

2-amino-4-{[(benzyloxy)carbonyl]amino}-4-oxobutanoic acid

36.

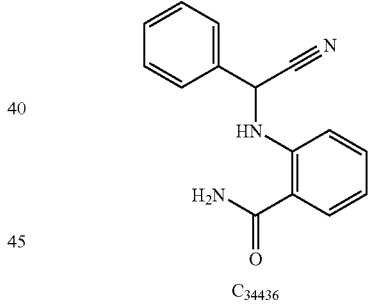

C₃₄₄₃₆

2-{[cyano(phenyl)methyl]amino}benzamide

37.

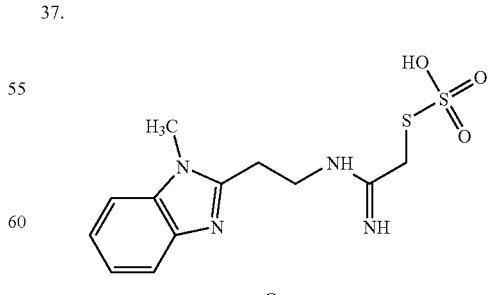

C₃₄₄₃₇

S-(2-imino-2-{[2-(1-methyl-1H-benzimidazol-2-yl)ethyl]amino}ethyl) hydrogen thiosulfate

38.

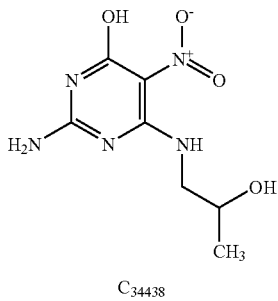

C34438

2-amino-6-[(2-hydroxypropyl)amino]-5-nitropyrimidin-4-ol

39.

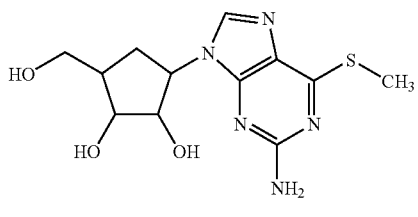

C34439

3-[2-amino-6-(methylthio)-9H-
purin-9-yl]-5-(hydroxymethyl)cyclopentane-1,2-diol

40.

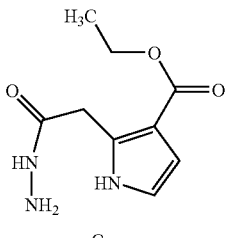

C34440 ethyl 2-(2-hydrazino-2-oxoethyl)-1H-pyrrole-3-carboxylate

The aforementioned molecules were described for the claimed function by the exhaustive molecular modelling of the consensus phosphorylation site, well defined for this enzyme (Meggio F., Pinna L. A. (2003) One-thousand-and-one substrates of protein kinase CK2. The FASEB J. 17:349-368), its validation by molecular binding to the CK2 enzyme, and further analysis by massive molecular screening of a chemical diversity database generated in our laboratory with an approximate number of one million two hundred thousand compounds.

The invention also includes any homologous variant of the described compounds. Defining as homologous variant, any molecule of similar or dissimilar chemical nature of those hereby described, but with a chemical structure allowing them to wield the same effects of the compounds hereby described with the resulting action of inhibiting the CK2 mediated phosphorylation of any CK2 substrate.

In another, but preferred realization of the invention, a pharmaceutical composition comprising one or more of the chemical compounds, and/or their pharmaceutically acceptable salts thereof, alone or along with other pharmaceutically allowed vehicles or additives. Also it is part of the present invention the use of the described chemical compounds, in the manufacture of medicines for the inhibition of the proliferation of the tumour cells in vitro, in vivo or in body associated devices, for the treatment in living organisms of cancer and/or other conditions in which the CK2 enzyme could have a pathological role.

The described chemical molecules were defined by their capacity to inhibit the phosphorylation of the minimal amino acid sequence S/T-X-X-E/D being X some amino acid preferably different from Lysine or Arginine, and furthermore other proteins not having such consensus sequence, binding to this type of compounds and having their CK2 mediated phosphorylation inhibited by them.

For the definition of chemical compounds described on this invention the authors have performed the exhaustive molecular modelling of the consensus phosphorylation site, well defined for this enzyme (Meggio F., Pinna L. A. (2003) One-thousand-and-one substrates of protein kinase CK2. The FASEB J. 17:349-368), its validation by molecular binding to the CK2 enzyme, and further analysis by massive molecular screening of a chemical diversity database generated in our laboratory with an approximate number of one million two hundred thousand compounds.

All compounds with calculated binding energy values above the average, were selected as positives in the first round, and submitted to a second round of screening with more restrictive selection values, and further analyzed to extract the structural regularities, the chemical structure of the compounds selected in the second screening round, was optimized to attain the highest possible values for the calculated binding energy. The resulting compounds were synthesized, purified using High Performance Liquid Chromatography, analyzed by Infrared Spectroscopy, Mass Spectrometry and Nuclear Magnetic Resonance and finally evaluated for their effectiveness in vitro and in vivo. According with this invention, the described chemical compounds are equally efficient on the capacity to inhibit the CK2 mediated phosphorylation event.

The chemical compounds described in this invention elicit cytotoxicity in human tumour cells, on a dose dependent manner, without the need of association with any cell penetration agent. Such evidence is in agreement with previous findings showing that chemical molecules on their own are able to be transported by the cellular machinery, and reach their targets, in the inside of the cells. (Meggio F, Pagano M A, et al. (2004) Inhibition of protein kinase CK2 by condensed polyphenolic derivatives. An in vitro and in vivo study. Biochemistry. 43:12931-12936).

Equally it is very appealing to find the IC50 values for the in vitro cytotoxicity studies of the chemical compounds in the nanomolar range. Those results show an enhanced cytotoxic activity of the hereby described compounds with respect to the previously reported cyclic peptides as inhibitors on the CK2 phosphorylation domain. In agreement with the in vitro results, the chemical compounds on this invention have a potent antitumoral effect when administered locally as well as systemically. Equally it was proven that the chemical compounds on this invention exert an antitumoral effect in dosage as low as 0.5 and 2 mg/Kg, representing in a 10 to 20 fold reduction on the described dosage for the previously described cyclic peptides.

BRIEF DESCRIPTION OF THE DRAWINGS

FIG. 1: Antitumoral effect of the chemical compounds in mice implanted human tumour models.

DETAILED DESCRIPTION OF PARTICULAR EMBODIMENTS/EXAMPLES

The preset invention is explained trough the following examples:

Example 1

Selection of the Compounds by In Silico Molecular Modelling

By using a computational model, developed by massive virtual screening, several compounds were selected based in a high values for the calculated binding energy of the receptor-ligand complex, as shown in the following table. This approximated energy value is estimated taking into account an exhaustive analysis of the conformation and several energetic components, using a computational program developed in our laboratory.

TABLE 1

Calculated Interaction Energies for the receptor-ligand complex.

| Chemical compound | Calculated energy - kJ mol$^{-1}$ |
|---|---|
| Peptide P15 | NA |
| C30401 | 37.5 |
| C30402 | 38.2 |
| C30403 | 40.1 |
| C30404 | 40.6 |
| C30405 | 39.8 |
| C30406 | 36.3 |
| C30407 | 32.4 |
| C30408 | 37.6 |
| C30409 | 41.2 |
| C30410 | 40.7 |
| C30411 | 38.2 |
| C30412 | 35.5 |
| C30413 | 32.6 |
| C30414 | 30.1 |
| C30415 | 34.7 |
| C31416 | 38 |
| C31417 | 32.1 |
| C31418 | 32.6 |
| C31419 | 31.4 |
| C31420 | 30 |
| C31421 | 34.6 |
| C31422 | 34.6 |
| C31423 | 32.8 |
| C31424 | 32.8 |
| C32425 | 41.6 |
| C33426 | 30 |
| C33427 | 39.5 |
| C34428 | 32.8 |
| C34429 | 31.4 |
| C34430 | 32.6 |
| C34431 | 31.4 |
| C34432 | 31.6 |
| C34433 | 34.4 |
| C34434 | 35.1 |

TABLE 1-continued

Calculated Interaction Energies for the receptor-ligand complex.

| Chemical compound | Calculated energy - kJ mol$^{-1}$ |
|---|---|
| C34435 | 34.8 |
| C34436 | 34.1 |
| C34437 | 33.8 |
| C34438 | 30.9 |
| C34439 | 40.6 |
| C34440 | 38.9 |

Example 2

Effect of the Described Chemical Compounds on the Phosphorylation of a Typical CK2 Substrate The assay consists in performing an in vitro phosphorylation reaction, using as the substrate the oncoprotein E7 from Human Papilloma Virus type 16 (VHP-16) expressed in *E. coli* as a Glutathione S-Transferase (GST) fusion protein. The resulting E7-GST is then purified by Glutathione-Sepharose (Pharmacia) affinity chromatography. Before the enzymatic reaction E7-GST was preincubated one hour at 37° C., with different concentrations of the chemical compounds. The reaction is carried out in a mixture consisting of 50 µl Tris: HCL 25 mM pH 7.5 buffer, 1 µCi of $^{32}$P-γATP, 100 µM ATP, 40 µl E7-GST containing resin, 0.2 M NaCl, 10 mM MgCl and 1 unit of the CK2 enzyme (Promega), allowing it to proceed for 40 minutes at 37° C. After the reaction the resin is washed three times with 0.5 ml of the reaction buffer and finally the phosphorylation level of E7-GST is analyzed in a 10% polyacrylamide gel electrophoresis (PAGE). The visualization of the phosphorylated protein is carried out by exposing X-ray sensitive films to the dried PAGE gel, and the quantification was done by densitometry analysis of the films. The IC50 values were estimated using each dosage-effect curve. The IC50 values are considered as the inhibitory concentration affecting the 50% of the enzyme activity. In parallel a control experiment was included as a comparison, assaying in the same conditions the cyclic peptide P15 reported before as inhibitor for the CK2 substrate phosphorylation site.

Table 2 results indicate that the chemical compounds described herein are effective inhibitors for a typical CK2 substrate, as deemed from the IC50 values. A remarkable fact is to notice the highest inhibitory capacity of the chemical compounds compared with the previously reported cyclic peptide, only active in the micromolar range.

TABLE 2

Inhibitory effect on a CK2 typical substrate

| Chemical compound | Inhibitory concentration 50 (IC50) nM |
|---|---|
| Peptide P15 | 2 000 ± 20 |
| C30401 | 26 ± 11 |

TABLE 2-continued

Inhibitory effect on a CK2 typical substrate

| Chemical compound | Inhibitory concentration 50 (IC50) nM |
|---|---|
| C30402 | 30 ± 5 |
| C30403 | 34 ± 9 |
| C30404 | 20 ± 8 |
| C30405 | 27 ± 10 |
| C30406 | 32 ± 7 |
| C30407 | 22 ± 10 |
| C30408 | 29 ± 2 |
| C30409 | 31 ± 6 |
| C30410 | 40 ± 9 |
| C30411 | 27 ± 10 |
| C30412 | 30 ± 3 |
| C30413 | 24 ± 9 |
| C30414 | 23 ± 9 |
| C30415 | 33 ± 8 |
| C31416 | 39 ± 6 |
| C31417 | 28 ± 11 |
| C31418 | 32 ± 5 |
| C31419 | 30 ± 4 |
| C31420 | 25 ± 7 |
| C31421 | 30 ± 8 |
| C31422 | 24 ± 5 |
| C31423 | 26 ± 8 |
| C31424 | 32 ± 13 |
| C32425 | 35 ± 3 |
| C33426 | 29 ± 8 |
| C33427 | 31 ± 7 |
| C34428 | 25 ± 7 |
| C34429 | 21 ± 12 |
| C34430 | 30 ± 4 |
| C34431 | 32 ± 6 |
| C34432 | 29 ± 7 |
| C34433 | 26 ± 10 |
| C34434 | 28 ± 5 |
| C34435 | 34 ± 3 |
| C34436 | 30 ± 2 |
| C34437 | 27 ± 4 |
| C34438 | 31 ± 1 |
| C34439 | 33 ± 5 |
| C34440 | 26 ± 4 |

Example 3

Effect of the Described Chemical Compounds on the Phosphorylation of the CK2 Consensus Site The assay consists in performing an in vitro phosphorylation reaction, using as the substrate the sequence RRREEE-TEEE (SEQ. ID NO. 1) widely accepted as an optimized consensus phosphorylation domain for the CK2 substrates.

Before the enzymatic reaction the substrate peptide was preincubated one hour at 37° C., with different concentrations of the chemical compounds. The reaction is carried out in a mixture consisting of 50 µl Tris:HCL 25 mM pH 7.5 buffer, 1 µCi of $^{32}P$-γATP, 100 µM ATP, 40 µl E7-GST containing resin, 0.2 M NaCl, 10 mM MgCl and 1 unit of the CK2 enzyme (Promega), allowing it to proceed for 10 minutes at 37° C. After the reaction 5 µl of the reaction mixture were applied to a Whatmann PE-81 paper filter and washed four times with 10 mM $H_3PO_4$, finally the paper associated radio-activity was measured and the cpm value for each sample was directly correlated with the CK2 enzymatic activity.

The IC50 values were estimated using each dosage-effect curve. The IC50 values are considered as the inhibitory concentration affecting the 50% of the enzyme activity. In parallel a control experiment was included as a comparison, assaying in the same conditions the cyclic peptide P15 reported before as inhibitor for the CK2 substrate phosphorylation site.

Table 3 results indicate that the chemical compounds described herein are effective inhibitors for a typical CK2 substrate, as deemed from the IC50 values. A remarkable fact is to notice the highest inhibitory capacity of the chemical compounds compared with the previously reported cyclic peptide, only active in the micromolar range.

TABLE 3

Inhibitory effect on the CK2 optimized consensus substrate sequence.

| Chemical compound | Inhibitory concentration 50 (IC50) nM |
|---|---|
| Peptide P15 | 5 000 ± 162 |
| C30401 | 62 ± 11 |
| C30402 | 74 ± 7 |
| C30403 | 58 ± 9 |
| C30404 | 61 ± 8 |
| C30405 | 57 ± 10 |
| C30406 | 60 ± 7 |
| C30407 | 73 ± 11 |
| C30408 | 79 ± 5 |
| C30409 | 55 ± 6 |
| C30410 | 54 ± 7 |
| C30411 | 66 ± 12 |
| C30412 | 71 ± 5 |
| C30413 | 64 ± 11 |
| C30414 | 68 ± 9 |
| C30415 | 72 ± 10 |
| C31416 | 69 ± 6 |
| C31417 | 78 ± 11 |
| C31418 | 72 ± 5 |
| C31419 | 60 ± 8 |
| C31420 | 55 ± 11 |
| C31421 | 50 ± 8 |
| C31422 | 74 ± 5 |
| C31423 | 76 ± 4 |
| C31424 | 62 ± 1 |
| C32425 | 65 ± 13 |
| C33426 | 79 ± 9 |
| C33427 | 51 ± 7 |
| C34428 | 65 ± 10 |
| C34429 | 61 ± 4 |
| C34430 | 70 ± 4 |
| C34431 | 55 ± 3 |
| C34432 | 67 ± 7 |
| C34433 | 76 ± 8 |
| C34434 | 78 ± 1 |
| C34435 | 64 ± 6 |
| C34436 | 66 ± 2 |
| C34437 | 71 ± 9 |
| C34438 | 81 ± 7 |
| C34439 | 63 ± 12 |
| C34440 | 56 ± 4 |

Example 4

Effect of the Chemical Compounds Descried Herein on Human Tumour Cells

H-125 cells from a human Non Small Cells Lung Carcinoma were soiled in 96 well plates (Costar) to a $2 \times 10^4$ cell/ml density in Dulbecco (DMEM) media (Gibco) and supplemented with Foetal Calf Serum (Gibco). 24 hours later the chemical compounds described herein were added to the cultured media in a range between 0.5 and 100 nM, incubating the mixture for 72 h at 37° C. in 5% $CO_2$, at the end 20 μl of a 1.90 mg/ml MTS solution was added. The plates were kept 1 additional hour on the same incubation conditions and the absorbance at 492 nm was read. The results are evaluated as growth percentage to controls without any compound, and the IC50 values were estimated using each dosage-effect curve. The IC50 values are considered as the inhibitory concentration affecting the 50% of the enzyme activity. In parallel a control experiment was included as a comparison, assaying in the same conditions the cyclic peptide P15 reported before as inhibitor for the CK2 substrate phosphorylation site.

Table 4 results indicate that the chemical compounds described herein have a potent in vitro cytotoxic effect on cultured human tumour cells, as deemed from the IC50 values. A remarkable fact is to notice the highest inhibitory capacity of the chemical compounds compared with the previously reported cyclic peptide, only active in the micromolar range.

TABLE 4

Cytotoxic effect on cultured human tumour cells.

| Chemical compound | Inhibitory concentration 50 (IC50) nM |
| --- | --- |
| Peptide P15 | 70 000 ± 562 |
| C30401 | 103 ± 21 |
| C30402 | 98 ± 7 |
| C30403 | 128 ± 9 |
| C30404 | 115 ± 18 |
| C30405 | 104 ± 12 |
| C30406 | 97 ± 17 |
| C30407 | 103 ± 11 |
| C30408 | 119 ± 8 |
| C30409 | 104 ± 6 |
| C30410 | 114 ± 7 |
| C30411 | 126 ± 15 |
| C30412 | 91 ± 15 |
| C30413 | 130 ± 11 |
| C30414 | 118 ± 9 |
| C30415 | 112 ± 10 |
| C31416 | 109 ± 6 |
| C31417 | 118 ± 21 |

TABLE 4-continued

Cytotoxic effect on cultured human tumour cells.

| Chemical compound | Inhibitory concentration 50 (IC50) nM |
| --- | --- |
| C31418 | 123 ± 15 |
| C31419 | 132 ± 18 |
| C31420 | 125 ± 10 |
| C31421 | 120 ± 18 |
| C31422 | 114 ± 5 |
| C31423 | 106 ± 9 |
| C31424 | 162 ± 11 |
| C32425 | 115 ± 12 |
| C33426 | 109 ± 19 |
| C33427 | 151 ± 7 |
| C34428 | 165 ± 12 |
| C34429 | 131 ± 4 |
| C34430 | 140 ± 14 |
| C34431 | 155 ± 23 |
| C34432 | 127 ± 7 |
| C34433 | 116 ± 18 |
| C34434 | 108 ± 21 |
| C34435 | 124 ± 16 |
| C34436 | 116 ± 22 |
| C34437 | 131 ± 9 |
| C34438 | 111 ± 17 |
| C34439 | 123 ± 25 |
| C34440 | 136 ± 32 |

Example 5

Antitumoral Effect on Nude Mice Implanted Human Tumours Models

Female BalbC nude mice between 6 to 8 weeks of age were used for this assay. For the tumour implant on this model 5 000 000H-125 cells resuspended in 250 μl PBS were injected in the dorsal region of the animals. Once the tumours were palpable with an approximated volume of 50 $mm^3$, a direct daily administration of 200 μg of compounds C32425, C33426 and C33427 was performed for 5 days. As shown in FIG. 1 the administration of the chemical compounds resulted in a significant antitumoral response. Such results indicate that the chemical compounds inhibiting the CK2 mediated phosphorylation are able to elicit antitumoral response in a relevant model for the Experimental Oncology.

The invention claimed is:

1. A method of treating a neoplastic disease or condition mediated by CK2 comprising administering a pharmaceutical composition consisting essentially of one or more chemical compounds shown below:

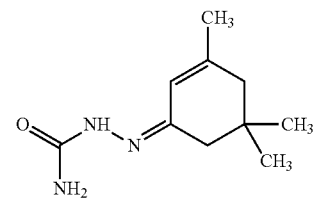

c30401
(1Z)-3,5,5-trimethylcyclohex-
2-en-1-one semicarbazone

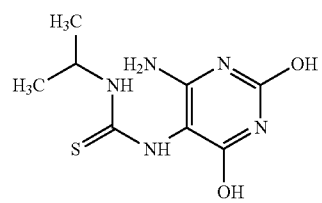

c30402
N-(4-amino-2,6-dihydroxypyrimidin-
5-yl)-N-isopropylthiourea

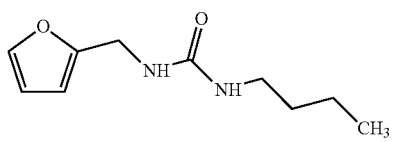

c30403
N-butyl-N-(2-furylmethyl)urea

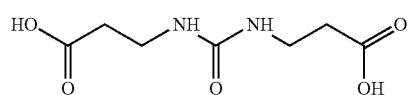

c30404
3-({[(2-carboxyethyl)amino]carbonyl}amino)
propanoic acid

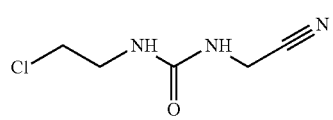

c30405
1-(2-chloroethyl)-3-cyanomethyl)urea

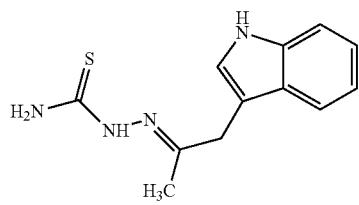

c30406
(2E)-1-(1H-indol-3-yl)acetone
thiosemicarbazone

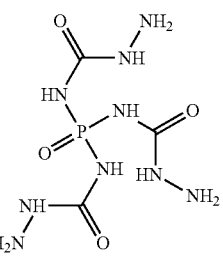

c30407
N,N,N'-phosphoryltrihydrazinecarboxamide

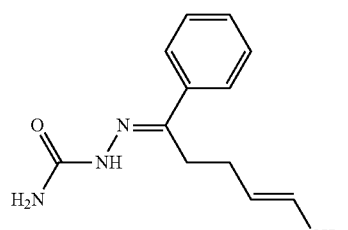

c30408
(1E,4E)-1-phenylhex-4-en-1-one
semicarbazone

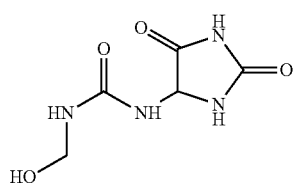

c30409
1-(2,5-dioxoimidazolidin-4-yl)-3-
(hydroxymethyl)urea

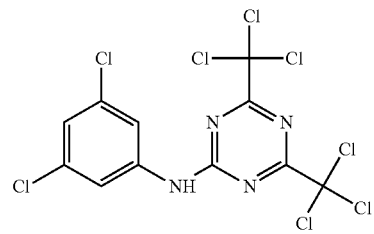

c30410
N-(3,5-dichlorophenyl)-4,6-bis(trichloromethyl)-
1,3,5-triazin-2-amine

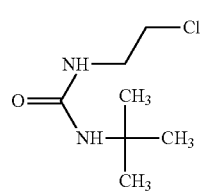

c30411
1-tert-butyl-3-(2-chloroethyl)urea

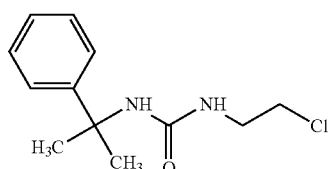

c30412
1-(2-chloroethyl)-3(1-methyl-
1-phenylethyl)urea

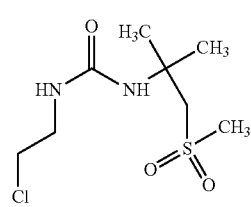

c30413
1-(2-chloroethyl)-3(1,1-dimethyl-
2-(methylsulfonyl)ethyl]urea

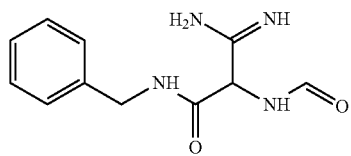

c30414
3-amino-N-benzyl-2-(formylamino)-
3-iminopropanamide

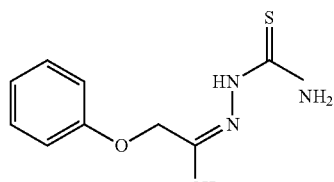

c30415
(2Z)-1-phenoxyacetone
thiosemicarbazone

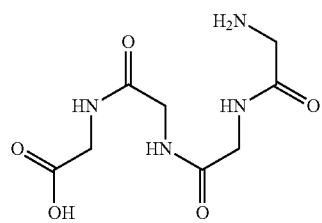

c31416
{[({[(aminoacetyl)amino]acetyl}amino)
acetyl]amino}acetic acid

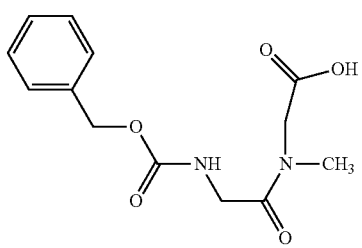

c31417
[({[(benzyloxy)carbonyl]amino}
acetyl)(methyl)amino]acetic acid

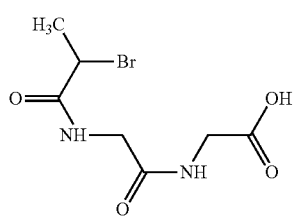

c31418
({[(2-bromopropanoyl)amino]
acetyl}amino)acetic acid

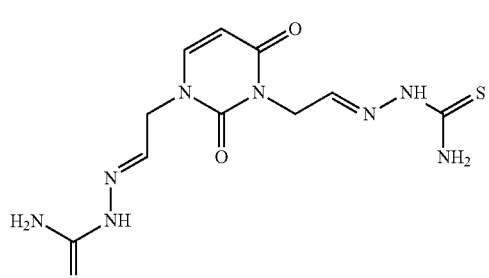

c31419
(1E,1'E)-2,2'-(2,4-dioxopyrimidine-1,3(2H,4H)-
diyl)diacetaldehyde dithiosemicarbazone

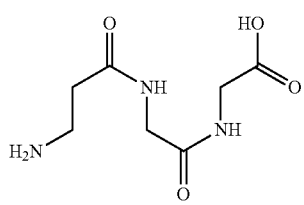

c31420
({[(3-aminopropanoyl)amino]acetyl}amino)acetic acid

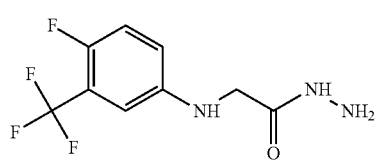

c31421
2-{[4-fluoro-3-(tirfluoromethyl)phenyl]
amino}acetohydrazide

-continued

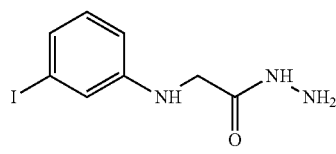

c31422
2-[(3-iodophenyl)
amino]acetohydrazide

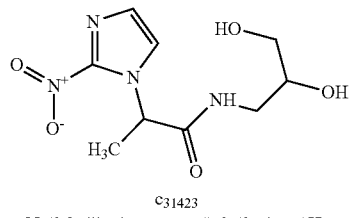

c31423
N-(2,3-dihydroxypropyl)-2-(2-nitro-1H-
imidazol-1-yl)propanamide

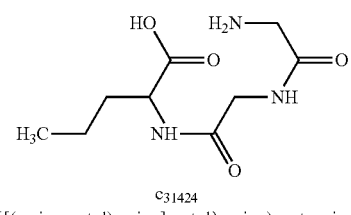

c31424
2-({[(aminoacetyl)amino]acetyl}amino)pentanoic acid

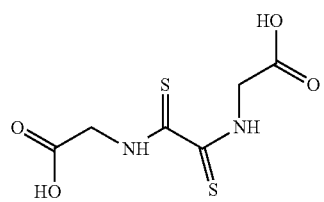

c31425
2,2'-[(1,2-dithioxoethane-1,2-diyl)diimino]
diacetic acid

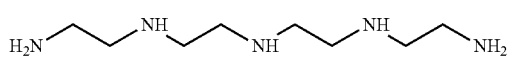

c33426
N-(2-aminoethyl)-N'-{2-[(2-aminoethyl)amino]ethyl}
ethane-1,2-diamine

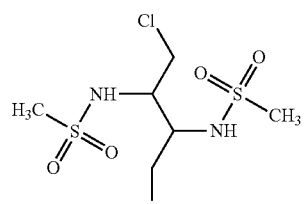

c33427
N,N-(1,4-dichlorobutane-2,3-diyl)
dimethanesulfonamide

-continued

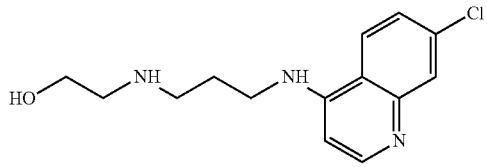

c34428
2-({3-[(7-chloroquinolin-4-yl)amino]propyl}
amino)etahnol

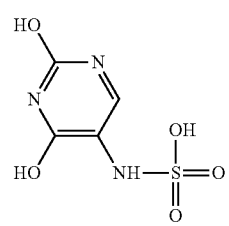

c34429
(2,4-dihydroxypyrimidin-5-yl)
sulfamic acid

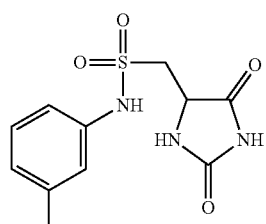

c34430
1-(2,5-dioxoimidazolidin-4-yl)-N-[3-
(trifluoromethyl)phenyl]methanesulfonamide

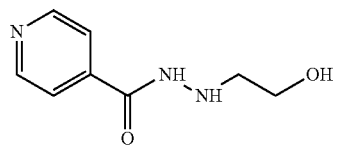

c34431
N-(2-hydroxyethyl)isonicotinohyrazide

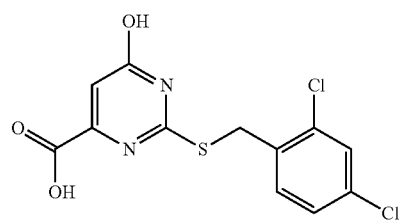

c34432
2-[(2,4-dichlorobenzyl)thio]-6-hydroxypyrimidine-
4-carboxylic acid

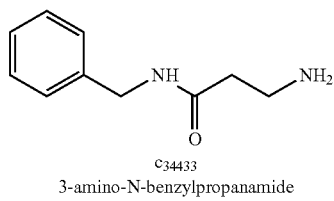

c34433
3-amino-N-benzylpropanamide

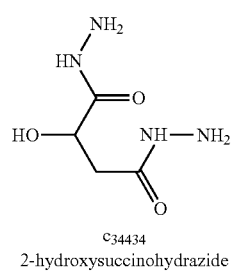

c34434
2-hydroxysuccinohydrazide

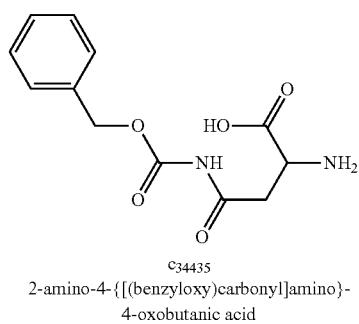

c34435
2-amino-4-{[(benzyloxy)carbonyl]amino}-
4-oxobutanic acid

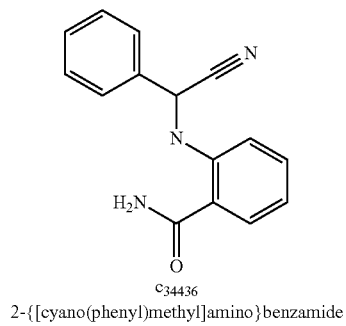

c34436
2-{[cyano(phenyl)methyl]amino}benzamide

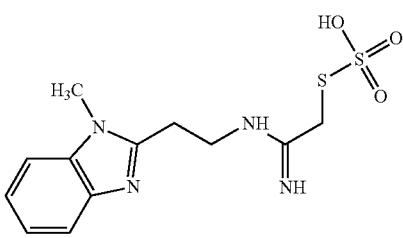

c34437
S-(2-imino-2-{[2-(1-methyl-1H-benzimidazol-2-yl)
ethyl]amino}ethyl hydrogen thiosulfate

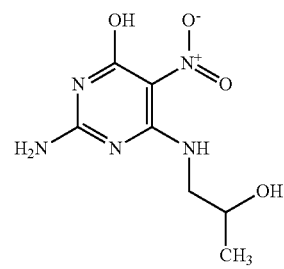

c34438
2-amino-6-[(2-hydroxypropyl)
amino]-5-nitropyrimidin-4-ol

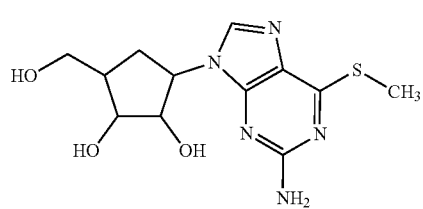

c34439
3-[2-amino-6-(methylthio)-9H-purin-9-yl]-
5-(hydroxymethyl)cyclopentane-1,2-diol and

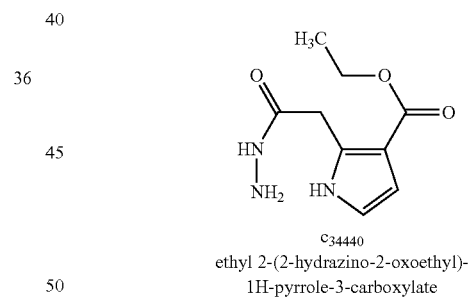

c34440
ethyl 2-(2-hydrazino-2-oxoethyl)-
1H-pyrrole-3-carboxylate to a subject in need thereof.

2. A method according to claim 1, wherein the disease or condition is cancer.

* * * * *

UNITED STATES PATENT AND TRADEMARK OFFICE
CERTIFICATE OF CORRECTION

| | | |
|---|---|---|
| PATENT NO. | : 8,748,411 B2 | Page 1 of 1 |
| APPLICATION NO. | : 11/920031 | |
| DATED | : June 10, 2014 | |
| INVENTOR(S) | : Fernandez et al. | |

It is certified that error appears in the above-identified patent and that said Letters Patent is hereby corrected as shown below:

On the title page, item [57]

Line 9:

Replace: "neoplasic processes."
  With: --neoplastic processes.--

Signed and Sealed this
Eleventh Day of November, 2014

Michelle K. Lee
*Deputy Director of the United States Patent and Trademark Office*

SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 1

Arg Arg Arg Glu Glu Glu Thr Glu Glu Glu
1               5                   10